(12) United States Patent
Marasco, Jr.

(10) Patent No.: US 6,562,013 B1
(45) Date of Patent: May 13, 2003

(54) KIT ASSEMBLY FOR COMPLETE WOUND TREATMENT

(75) Inventor: Patrick V. Marasco, Jr., Boxford, MA (US)

(73) Assignee: PulseCare Medical LLC, North Andover, MA (US)

( * ) Notice: Subject to any disclaimer, the term of this patent is extended or adjusted under 35 U.S.C. 154(b) by 0 days.

(21) Appl. No.: 09/561,978

(22) Filed: May 2, 2000

Related U.S. Application Data

(60) Continuation-in-part of application No. 09/156,115, filed on Sep. 18, 1998, now Pat. No. 6,083,209, which is a division of application No. 08/682,888, filed on Jul. 11, 1996, now Pat. No. 5,848,998.

(51) Int. Cl.$^7$ .............................................. A61M 35/00
(52) U.S. Cl. ......................... 604/290; 604/289; 604/23; 128/202.12
(58) Field of Search .......................... 604/23, 319, 289, 604/356, 408, 290, 293, 390, 320; 600/21; 128/202.12, DIG. 24; 606/313

(56) References Cited

U.S. PATENT DOCUMENTS

| | | | | |
|---|---|---|---|---|
| 3,744,491 A | * | 7/1973 | Fischer | 604/23 |
| 3,969,038 A | * | 7/1976 | Nonnenmacher et al. | 417/218 |
| 4,003,371 A | * | 1/1977 | Fischer | 601/44 |
| 5,312,385 A | * | 5/1994 | Greco | 128/DIG. 24 |
| 5,344,433 A | * | 9/1994 | Talmore | 607/88 |
| 5,447,504 A | * | 9/1995 | Baker et al. | 601/166 |
| 5,730,479 A | * | 3/1998 | Jansson | 294/15 |
| 2001/0049511 A1 | * | 12/2001 | Coleman et al. | 604/290 |

* cited by examiner

Primary Examiner—Dennis Ruhl
Assistant Examiner—Linh Truong
(74) Attorney, Agent, or Firm—Don Halgren

(57) ABSTRACT

The present invention is a wound treatment kit assembly for the washing, cleansing, medicinal treatment and maintenance of a wound side on the limb or torso of a patient. The kit has a plurality of flexible body component-treating bag-like envelopes, attachable to a body component; a hand manipulable fluid delivery gun; a plurality of wand-like conduits having a first end for connective attachment to the fluid delivery gun and a second end for entry into the bag-like envelope; a fluid reservoir; and a plurality of flexible delivery conduits for conducting fluid from the reservoir to the hand manipulable gun when bag-like envelope is secured to a component of a patient and the gun is in fluid communication with the bag-like envelope.

12 Claims, 2 Drawing Sheets

KIT ASSEMBLY FOR COMPLETE WOUND TREATMENT

BACKGROUND OF THE INVENTION

Field of the Invention

This invention relates to the treatment of wounds and more particularly to a kit apparatus for improving the treatment of such wounds, and is a continuation-in-part application of my U.S. patent application Ser. No. 09/156,115, filed Sep. 18, 1998 now U.S. Pat. No. 6,083,209 titled "Tissue Debriding Apparatus" which is a divisional application of U.S. patent application Ser. No. 08/682,888, filed Jul. 11, 1996, now U.S. Pat. No. 5,848,998, titled "Tissue Debriding Apparatus", each application being incorporated by reference in their entirety.

PRIOR ART

Wound management is a significant portion of all medical practice today. Wounds typically occur from a bum, a contaminated trauma (blunt trauma), chronic ulceration, tendon laceration, abscess cavity to be drained, cellulitus (skin irritation), open bone fracture (compound fracture), and pressure sores. Such wounds and their treatment constitute a large percentage of the treatment provided to medical patients. The best treatment or these wounds is complete as possible a cleansing and sterile treatment of them, as close to the time and site of injury, as possible.

The number of methods for wound cleansing and debridement have been developed over the past years. Those methods have been included wound cleansers such as povidone-iodine, hydrogen-peroxide, acetic acid, and chlorinated solutions, which however, have a cytotoxic effect on cells. Other types of wound cleaning and debridement include piston type syringe irrigation, whirlpool treatments, wet to dry saline gauze dressings, surgical/mechanical debridement, enzymatic debridement, absorbent dextranomor microbeads, and pulsed lavage.

Syringe irrigation is sufficient for cleaning most simple wounds. Large complicated wounds, however, require large quantities of irrigant for effective cleansing and debridement. Whirlpool treatments are often utilized for cleansing larger wounds and appear to be common in physical therapy departments. However, with certain deep wounds flushing and debridement is difficult to achieve. The patient must often be uncomfortably positioned in order to direct jets at the wound. If a patient is incontinent, or if multiple wounds are present, cross contamination between those multiple wounds may occur. Wet to dry saline gauze dressings are simple to use and are inexpensive for the patient, but in removal of that dressing they may also damage healthy tissue and may be painful. Such dressing changes may also be a labor intensive procedure. Also, wound care products which are applied as a viscous gel or alginate will require mechanical debridement of the gel between treatments. A complete system to minimize associated risk, to provide such tissue debridement and cleansing treatment at a hospital, field site or home, to a wound of a patient, is badly needed.

A relatively new procedure in wound management is includes pulsed lavage wherein a pulsating water jet is directed toward the wound site, which method is fairly effective in removing debris, bacteria or viscous gel type dressings from those wounds.

Pulse lavage irrigation devices typically utilize a cone shaped shield, having an open base which is placed over the wound. The shield is utilized to minimize splashing to protect the health care worker and to prevent aerosolization of body fluid. Typically a pan would be held against a lower portion of the skin of a patient being treated. A suction tube may be hung into the pan so as to drain out fluid. The fluid is typically saline or saline with an antibiotic added for wound debridement and sterilization.

A number of such physical devices are shown in the prior art to isolate and permit treatment of certain wound sites. One such device is shown in U.S. Pat. No. 5,447,504 to Baker et al. showing a misting apparatus which comprises a container secured to a limb of a patient at each end, by a rigid cuff. The cuff is held onto the limb by a securement strap and each cuff has an opening to permit an elongated listing tool to be fixedly arranged thereto. This apparatus may be satisfactory for applying a mist to a limb, for the prevention of that limb from drying out, but it has rigid conduits which puts limitations on the manipulability of the device which prevents it from applying a wide range of debriding and cleansing actions. U.S. Pat. No. 3,867,929 to Joyner et al. shows an ultrasonic treatment device in which an acoustically transparent container is wrapped around the limb containing a wound site. The container had ultrasonic transducers spaced therearound for generating acoustic vibrations through a fluid within the container and onto the wound site. This however does not provide the flushing necessary of many wound examples.

A further means for treating surface wounds is shown in U.S. Pat. No. 3,228,140 to McCarthy. This device includes cup-like housings which are placed against the wound site to permit containment of the spray from a nozzle and drainage therefrom as well.

Other interesting limb treatment devices are shown in U.S. Pat. Nos. 3,094,983 to Macleod, 2,113,253 to Gray, and 1,105,365 to McQuhae each showing an unusual containment for a limb to permit bathing or improve blood circulation therewithin. Each of these devices, however, are unduly complicated and are not conducive to efficient personalized and adaptive treatment either at hospital bedside without transportation to the physical therapy department, or at home or in the field on the wound of the patient. The prior art requires that the patients wound's conform to the apparatus, and not vice-versa. None of these teach the ability of a treatment kit for wound treatment to effect a complete "whirlpool-bath" type wound treatment, either in a patient's home or in a hospital, so as to otherwise eliminate the risk of transporting a patient to physical therapy or risk lifting the patient into a whirlpool bath, and certainly no provision for use in the field with similar treatment therapies.

It is thus an object of the present invention, to overcome the shortcomings of the prior art.

It is further object of the present invention to provide a complete, portable wound treatment kit apparatus which may be utilized in a medical facility, in a home, or in a field environment which kit apparatus is adaptable to a broad array of wound sites, and, which kit apparatus also permits the protection the operator as well as the patient being treated.

It is yet further object of the present invention, to provide a wound treatment kit apparatus which prevents cross contamination of a wound site from outside the environment or from other wound sites on that patient, and minimizes the likelihood of contamination from that patient to a further patient.

BRIEF SUMMARY OF THE INVENTION

The present invention comprises a kit apparatus for the washing and debridement of wounds on limbs and body portions of patients. Such a kit arrangement is anticipated to be used both in and outside a formal medical facility, such as for the use in a home or the field. This kit permits the replacement or minimization of the risk associated with the use of a whirlpool bath, to eliminate cross-contamination of body fluids, and to minimize the spread of bacteria, hepatitis, and other strep and pathogenic organisms. The kit arrangement of the present invention includes a plurality of bag-like flexible envelopes of transparent plastic material having a first primary opening for the receipt of a body limb or for the attachment to a body portion having a wound site thereon. The envelope will include at least one secondary opening having a flexible annular support collar therearound for insertion of a fluid delivery device. The flexible envelope will have at least one tertiary port for the drainage and withdrawal of fluid, washed away tissue, and for the release of pressurized gas which has been delivered into the envelope.

The kit arrangement includes a hand-held, reusable, manipulable gun for the delivery of a pressurized fluid. The fluid may be a gas and or a liquid mixture. The hand manipulable gun has a trigger mechanism to permit the regulation of the flow of fluid and of gas therefrom.

The kit also preferably contains a plurality of hollow, elongated tube-like wands, having a first end and a second end. The first end of each wand is insertable into a receiving orifice on the hand manipulable gun, and the second end of each wand having a nozzle attachment thereon. The nozzle attachment may include various angled nozzles, a brush, a sponge, or a medicament applicator. The kit also preferably includes a plurality of lengths of tubing to conduct gas or fluid from a reservoir or supply, to a handle of the hand manipulable gun so as to supply the material to be pumped therethrough.

Also preferably included in the kit apparatus, is a plurality of lengths of discharge-tubing, and a plurality of disposable waste bags. The discharge tubing is included, to be attached to a discharge nipple on the tertiary opening of the flexible baglike envelope. The kit of the present invention may contain medicaments for the washing, debridement, and treatment of the wound within the flexible envelope. The kit will also preferably include small canisters of compressed gas containing oxygen, carbon dioxide, hydrogen peroxide, growth factors and/or antibacterials which are useful for sterilization procedures and for enhancing wound heating.

The kit containing the elements cited hereinabove thus permits wound treatment by personnel or by the patient him/herself, even at remote sites from a medical facility. The flexible transparent envelope-like bag for encirclement of the wound, preferably has a mildly aggressive adhesive arranged on its peripheral edge, to act as a sealant around the periphery of the wound site. The primary opening may also have a collar or tightenable loop therearound to facilitate attachment of and securement of the envelope to the patient. The flexible bag permits long term wound treatment, to keep the wound from drying out, and keeps the wound area sterile once the debridement activity has been completed. The secondary and tertiary openings within the flexible bag may be sealed by a flap arrangement or by closing a valve therein.

In a further embodiment of the present invention, a plurality of flexible fiber optic cables may be arranged within the flexible envelope, to permit the delivery of an ultraviolet light from an ultraviolet light source outside the flexible bag to the wound site therewithin.

The invention thus comprises a wound treatment kit assembly for the washing, debriding, cleansing, medicinal treatment and maintenance of a wound site on the limb, scalp or torso of a patient comprising: a plurality of flexible body component-treating bag-like envelope, attachable to a body component; a hand manipulable fluid delivery gun with variable pressure capabilities because requirements for debridement will change during the various phases of wound healing; a pressure gage on the fluid delivery gun or bag or conduit to permit control of fluid pressure for each wound treatment phase; a plurality of wand-like conduits having a first end for connective attachment to the fluid delivery gun and a second end for entry into the bag-like envelope; a medicinal fluid reservoir; and a plurality of flexible delivery conduits for conducting fluid from the reservoir to the hand manipulable gun when bag-like envelope is secured to a component of a patient and the gun is in fluid communication with the bag-like envelope. The wound treatment kit assembly may include a plurality of nozzle attachments for securement to the second end of the wand once the second end of the wand has been inserted into the envelope and a plurality of flexible, disposable waste bags and a plurality of sections of discharge tubing so that fluid and body tissue matter drained from the bag-like envelope about a body component of a patient may be safely captured, sealed and disposed of without contamination to the patient or medical personnel. The wound treatment kit assembly preferably includes at least one canister of compressed gas for delivery of gas into the bag-like envelope through the delivery conduits, to provide sterility and maintain an inflation in the bag to permit the bag to be maintained at a spaced distance from a wound site therewithin, the plurality of nozzle attachments may include a brush, a sponge and a medicament applicator, and the kit assembly may include an optical cable and a power source to deliver light treatment through the cable and into the bag-like envelope for treating a body component therein. The adjustable pressure fluid delivery device may have an electrically powered pump to permit pressure adjustment and regulation of the fluid treatment stream onto the wound site. The pump is intended to be reusable and portable, with disposable tubing arranged therewith.

The invention also comprises a method of providing a wound cleansing, debridement and medical treatment delivery procedure to a patient outside of a medical facility, comprising the steps of: assembling a portable kit for remote wound care treatment, the kit including a fluid treatment delivery gun, including an adjustable fluid-pressure delivery device, a plurality of flexible bag-like body-component-enclosing envelopes, a fluid source, a plurality of conduits for delivery of fluid from the fluid source to the envelope in which a patient's body component is enclosed and for delivery of waste fluid from the envelope during the patient treatment process, providing a plurality of wand conduits for delivery of fluid from the gun into a port in said envelope, providing an optical fiber and a light source for the delivery of light treatment from the source into the envelope containing a body component of a patient.

Thus, what has been shown is a novel and unique kit arrangement to facilitate the treatment of wounds and to replace many wound treatment procedures and bathing arrangements found only in well-equipped medical facilities. The kit permits an all-inclusive assembly of apparatus to debride, wash, dry, and maintain a wound site sterile during its healing process, either in a medical facility, a home or in a field situation.

A BRIEF DESCRIPTION OF THE DRAWINGS

The objects and advantages of the present invention will become more apparent when viewed in conjunction with the following drawings in which.

DESCRIPTION OF THE PREFERRED EMBODIMENTS

Figure 1:
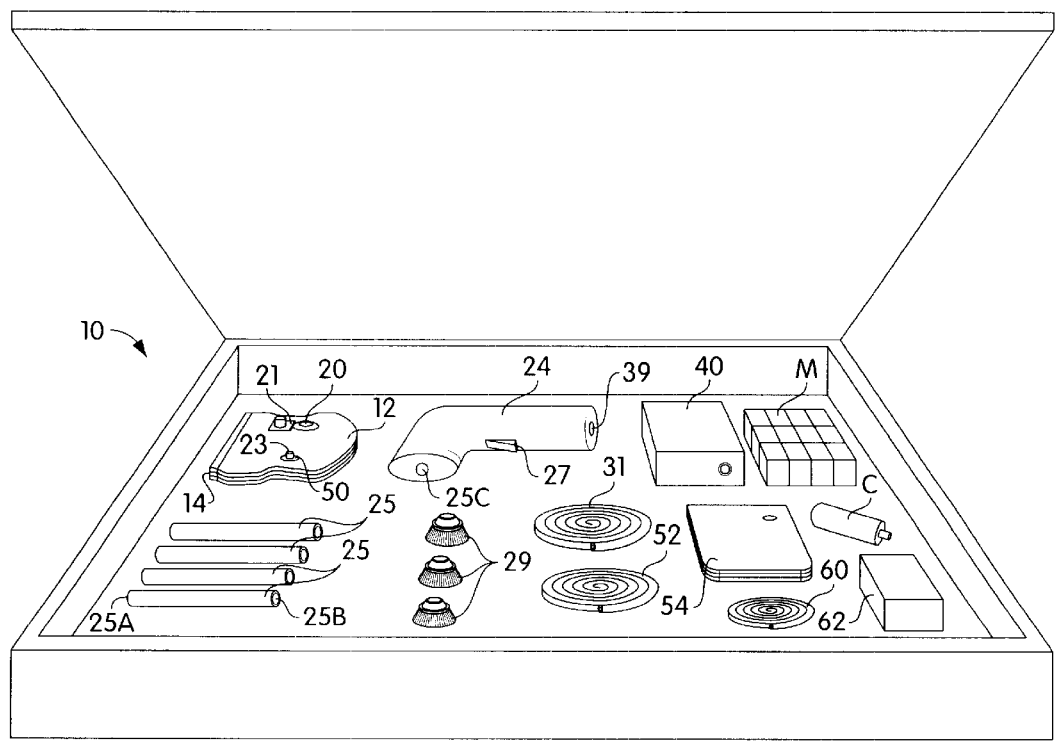
FIG. 1 is a perspective view of a kit assembly constructed according to the principles of the present invention.
Figure 2:
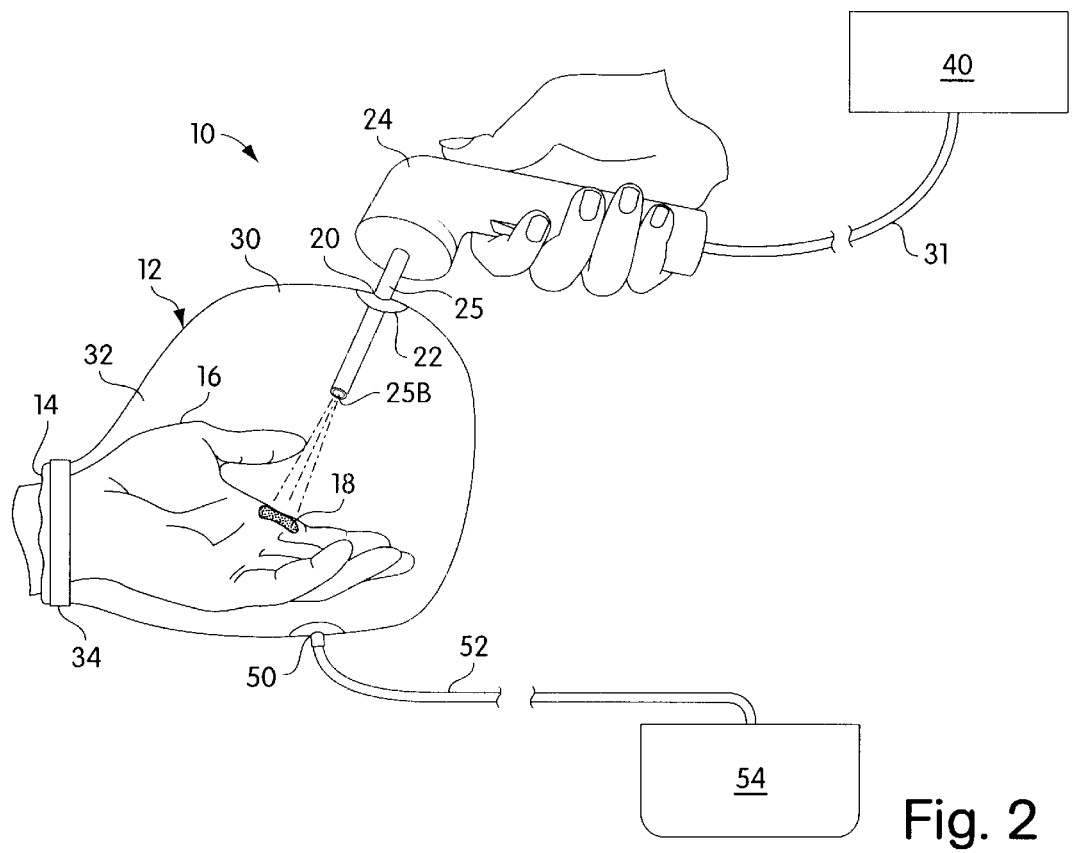
FIG. 2 is a side elevational view of a wound treatment shield and container of a kit assembly constructed according to the principles of the present invention, shown utilized on a body part and wound.
Figure 3:
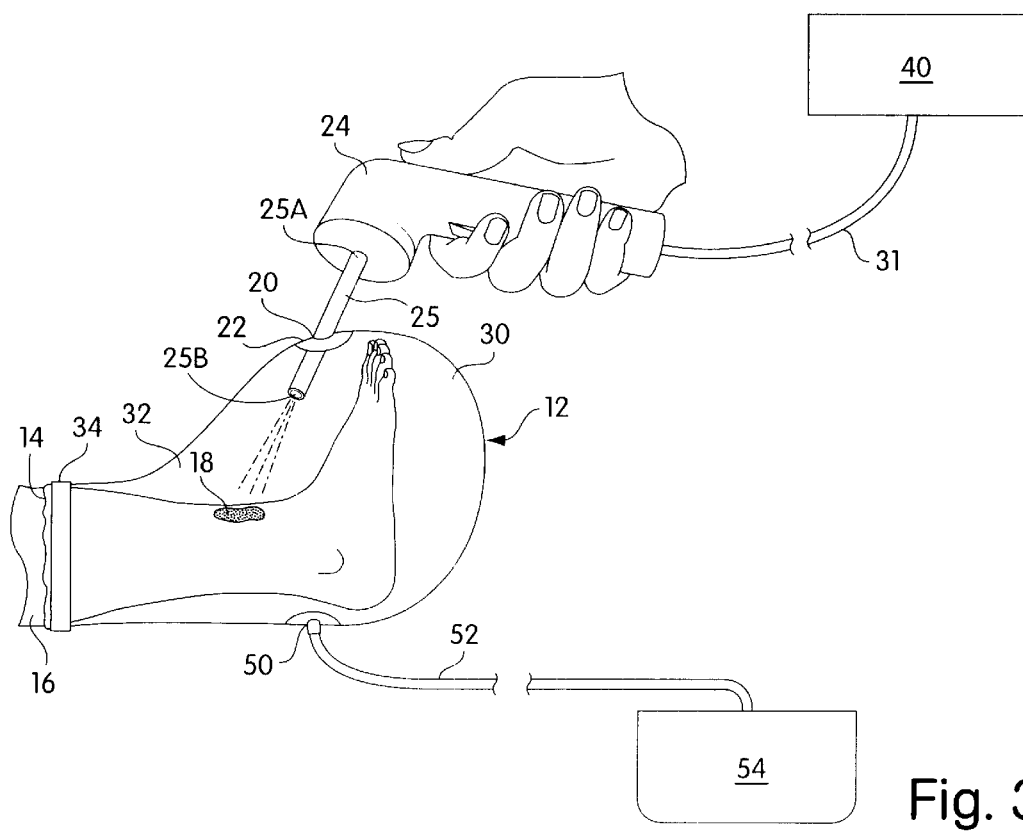
FIG. 3 is a side elevational view of the wound treatment shield and container of a kit assembly of the present invention, with an envelope arranged around the foot of a patient.

Referring now to the drawings in detail, and particularly to FIG. 1, there is shown the present invention which comprises a kit apparatus or assembly 10 for the washing and debridement of wounds on limbs and body portions of patients. Such a kit apparatus 10 is assembled to be most efficiently and properly used both in and outside a formal medical facility, such as for the use in a home or the field. This kit 10 permits the replacement or minimization of the use of cleansing such as a whirlpool bath, (which would not be available in a "field" application), and to eliminate cross-contamination of body fluids, and to minimize the spread of bacteria, hepatitis, and other strep and pathogenic organisms and avoid the risk associated with transporting a patient to and from a whirlpool bath and positioning that patient within the whirlpool bath. The kit arrangement 10 of the present invention includes a plurality of bag-like flexible envelopes 12 of transparent plastic material having a first primary opening 14 for the receipt of a body limb 16 or for the attachment to a body portion having a wound site 18 thereon, as exemplified in FIGS. 2 and 3. The envelope 12 will include an enlarged portion 30 and a narrowed portion 32 with at least one secondary opening 20 having a flexible annular support collar 22 therearound for insertion of a an adjustable-pressure fluid delivery device 24. The flexible envelope 12 will have at least one tertiary port 50 for the drainage and withdrawal of fluid, washed away tissue, and for the release of pressurized gas which has been delivered into the envelope 12.

The kit assembly 10 includes the adjustable-pressure fluid delivery device such as a hand manipulable gun 24 for the delivery of a pressurized fluid. The fluid may be a gas and or a liquid mixture. The hand manipulable gun 24 has a trigger mechanism 27 which controls an internal valve, to permit the regulation of the flow of fluid and of gas therefrom.

The kit assembly 10 may also preferably contain a plurality of hollow, elongated tube-like wands 25, having a first end 25A and a second end 25B. The first end 25A of each wand 25 is insertable into a receiving orifice 25C on the hand manipulable gun 24, and the second end 25B of each wand 25 having a nozzle attachment 29 thereon. The nozzle attachment 29 may include a brush, a sponge, or a medicament applicator. The kit 10 may also include a plurality of lengths of "medical grade" flexible supply tubing 31 to conduct gas or fluid from a reservoir or supply assembly 40, to a handle receiving orifice 39 of the hand manipulable gun 24 so as to supply the material to be pumped therethrough. The reservoir or supply assembly 40 may be comprised of a reusable, fluid pressure-adjustable pump and/or a suction apparatus to supply pressurized treatment fluid from the reservoir assembly 40 through the delivery gun 24 and to the wound site and withdraw it from the containment envelope or bag 12. The assembly 40 may also include a light and/or power source for use with the fluid delivery gun 24 and light treatment means associated therewith.

Also preferably included in the kit apparatus 10, is a plurality of lengths of flexible plastic discharge-tubing 52, and a plurality of disposable waste bags 54. The discharge tubing 52 is included, to be attached to a discharge nipple on the tertiary opening 50 of the flexible bag-like envelope 12. The kit 10 of the present invention preferably contains medicaments "M" for the washing, debridement, and treatment of the wound within the flexible envelope 12. The kit 10 in a further embodiment, also preferably includes a plurality of small canisters "C" of compressed gas containing oxygen, carbon dioxide, and or hydrogen peroxide which are useful for sterilization procedures.

The kit assembly 10 containing the primary elements cited hereinabove, permits wound treatment by personnel or by the patient him/herself at home or at sites remote from a medical facility. The flexible transparent envelope-like bag 12 for encirclement of the wound, preferably has a mildly aggressive adhesive arranged on the inner side of its peripheral edge of the primary opening 14, to act as a sealant around the periphery of the wound site. The primary opening 14 may also have a collar or tightenable loop 34 therearound to facilitate attachment of and securement of the bag or envelope 12 to the patient. The flexible bag 12 permits long term wound treatment, to keep the wound from drying out, and keeps the wound area sterile once the debridement activity has been completed. The secondary and tertiary openings 20 and 50 within the flexible bag 12 may be sealed by a flap arrangement 21 or by closing a valve 23 therein.

In a further embodiment of the present invention, a plurality of flexible fiber optic cables 60 are arranged within the flexible envelope 12, to permit the delivery of an ultraviolet light, from an ultraviolet light source 62 or within the outside the flexible bag 12 through the secondary opening 20, to the wound site therewithin. Such cables 60 may also be activated by a power or light source within the pump assembly 40.

Thus, what has been shown is a novel and unique kit assembly to facilitate the treatment of wounds in a hospital, at home or in the field, and to minimize risk and replace many wound treatment procedures found only in well-equipped medical facilities. The kit permits an all-inclusive assembly of apparatus necessary to debride, wash, dry, treat and maintain a wound site sterile during the multiple phases of the wound healing process.

I claim:

1. A wound treatment kit assembly for the washing, debriding, cleansing, medicinal treatment and maintenance of a wound site on the limb, scalp or torso of a patient comprising:

a plurality of flexible body component-treating bag-like pressurizably expandable envelopes, attachable to a body component;

a hand manipulable fluid delivery gun;

a plurality of wand-like conduits having a first end for connective attachment to said fluid delivery gun and a second end for entry into said bag-like envelopes;

a fluid reservoir;

a plurality of flexible delivery conduits for conducting fluid from said reservoir to said hand manipulable gun when said bag-like envelopes are secured to a component of a patient and said gun is in fluid communication with said bag-like pressurizably expandable envelopes, to provide complete wound treatment and minimize associated health risks commonly incurred with wound treatment; and at least one canister of compressed gas for delivery of gas into the bag-like pressurizably expandable envelope through said delivery conduits, to provide sterility, and maintain an inflation in said envelope to permit said envelopes to be maintained at a spaced distance from a wound site therewithin.

2. The wound treatment kit assembly as recited in claim 1, including a plurality of nozzle attachments for securement to said second end of said wand-like conduits once said second end of said wand has been inserted into said envelope.

3. The wound treatment kit assembly as recited in claim 2, including a plurality of flexible, disposable waste bags and a plurality of sections of discharge tubing so that fluid and body tissue matter drained from said bag like envelopes about a component of a patient may be safely captured and disposed of without contamination to the patient or medical personnel.

4. The wound treatment kit assembly as recited in claim 3, wherein said plurality of nozzle attachments includes a brush, a sponge and a medicament applicator.

5. The wound treatment kit assembly as recited in claim 1, wherein said fluid treatment delivery gun has a pressure adjustment arrangement to permit regulation of the flow of fluid onto said wound site as necessary during various phases of wound healing.

6. The wound treatment kit assembly as recited in claim 1, including an optical cable and a power source to deliver light treatment through said cable and into said bag-like envelopes for treating a body component therein.

7. A method of providing a wound cleansing, debridement and medical treatment delivery procedure to a patient outside of a medical facility, comprising the steps of:

assembling a portable kit for remote wound care treatment, said kit including a fluid treatment delivery gun, a plurality of flexible bag-like body-component-enclosing pressurizably expandable envelopes, a fluid source, a plurality of conduits for delivery of fluid from said fluid source to said pressurizably expandable envelopes in which a patient's body component is enclosed and for delivery of waste fluid from said envelope during the patient treatment; and providing an optical fiber and a light source for the delivery of light treatment from said light source into said envelope containing a body component of a patient.

8. The method as recited in claim 7, including the step of:
providing a plurality of wand conduits for delivery of fluid from said gun into a port in said envelope.

9. A wound treatment kit assembly for the washing, debriding, cleansing, medicinal treatment and maintenance of a wound site on the limb or torso of a patient comprising:

a plurality of flexible body component-treating bag-like pressurizably expandable envelopes, attachable to a body component;

a hand manipulable pressurizably adjustable fluid delivery gun;

a plurality of wand-like conduits having a first end for connective attachment to said fluid delivery gun and a second end for entry into said bag-like envelopes;

a fluid reservoir;

a plurality of flexible delivery conduits for conducting fluid from said reservoir to said hand manipulable gun when a bag-like envelope is secured to a component of a patient and said gun is in fluid communication with said bag-like envelopes;

a plurality of nozzle attachments for securement to said second end of said wand-like conduit once said second end of said wand-like conduit has been inserted into said envelopes;

a plurality of flexible, disposable waste bags and a plurality of sections of discharge tubing so that fluid and body tissue matter drained from said bag like envelope about a component of a patient may be safely captured and disposed of without contamination to the patient or medical personnel;

at least one canister of compressed gas for delivery of gas into the bag-like envelope through said delivery conduits, to provide sterility, and maintain an inflation in said bag to permit said pressurizably expandable envelope to be maintained at a spaced distance from a wound site therewithin, said plurality of nozzle attachments includes a brush, a sponge and a medicament applicator; and an optical cable and a power source to deliver light treatment through said cable and into said bag-like envelopes for treating a body component therein.

10. The wound treatment kit assembly for the washing, debriding, cleansing, medicinal treatment and maintenance of a wound site as recited in claim 9, including a pressure adjustable pump assembly for supplying pressurized wound treatment fluid through said fluid delivery gun and to said wound site.

11. The wound treatment kit assembly for the washing, debriding, cleansing, medicinal treatment and maintenance of a wound site as recited in claim 10, wherein said pressure adjustable pump includes a suction arrangement therewith, to also permit suctioned drainage of spent treatment fluid and debris from said bag-like envelope.

12. The wound treatment kit assembly for the washing, debriding, cleansing, medicinal treatment and maintenance of a wound site as recited in claim 11, wherein a light source and a power source are arranged within said pulp assembly.

* * * * *